United States Patent [19]

Matsumoto et al.

[11] Patent Number: 5,073,708
[45] Date of Patent: Dec. 17, 1991

[54] APPARATUS FOR INSPECTING THE PRESENCE OF FOREIGN MATTERS

[75] Inventors: Kunihiro Matsumoto; Masashi Aoki; Shuji Ohnaka; Hideshi Motonaga, all of Tokyo; Yukinobu Nishino, Ishikawa, all of Japan

[73] Assignee: Shibuya Kogyo Co., Ltd., Ishikawa, Japan

[21] Appl. No.: 578,779

[22] Filed: Sep. 7, 1990

[30] Foreign Application Priority Data

Sep. 11, 1989 [JP] Japan .................. 1-235986
Oct. 2, 1989 [JP] Japan .................. 1-257382

[51] Int. Cl.⁵ ............................................. G01N 9/04
[52] U.S. Cl. .................. 250/223 B; 356/427
[58] Field of Search ............ 250/223 B, 223 R; 356/427, 428, 240

[56] References Cited

U.S. PATENT DOCUMENTS

| | | | |
|---|---|---|---|
| 2,268,098 | 12/1941 | Weathers | 356/427 |
| 2,317,559 | 4/1943 | Stout | 356/427 |
| 2,331,277 | 10/1943 | Stout | 356/427 |
| 3,133,638 | 5/1964 | Calhoun | 209/82 |
| 3,811,567 | 5/1974 | Tomita et al. | 209/73 |
| 4,492,475 | 1/1985 | Takahashi | 356/427 |
| 4,680,463 | 7/1987 | Lutgendorf et al. | 250/223 B |
| 4,852,415 | 8/1989 | Bogatzki et al. | 250/223 B |

FOREIGN PATENT DOCUMENTS 47-10466 3/1972 Japan .
60-220850 11/1985 Japan .

Primary Examiner—David C. Nelms
Assistant Examiner—Que T. Le
Attorney, Agent, or Firm—Flynn, Thiel, Boutell & Tanis

[57] ABSTRACT

An apparatus for inspecting vessels for the presence of foreign matters inspects the vessel as it undergoes a reverse rotation which follows a forward rotation. A receptacle on which the vessel is driven for rotation is mounted on a rotatable body, and a receptacle is driven by a control motor for rotation in the forward and the reverse direction. A controller which controls the control motor detects any change in the speed of rotation of the rotatable body, and responds to such change by controlling the motor so that a given, predetermined permissible inspecting condition of the vessel is maintained during its forward and reverse rotation in the presence of a change in the speed of rotation of the rotatable body.

7 Claims, 5 Drawing Sheets

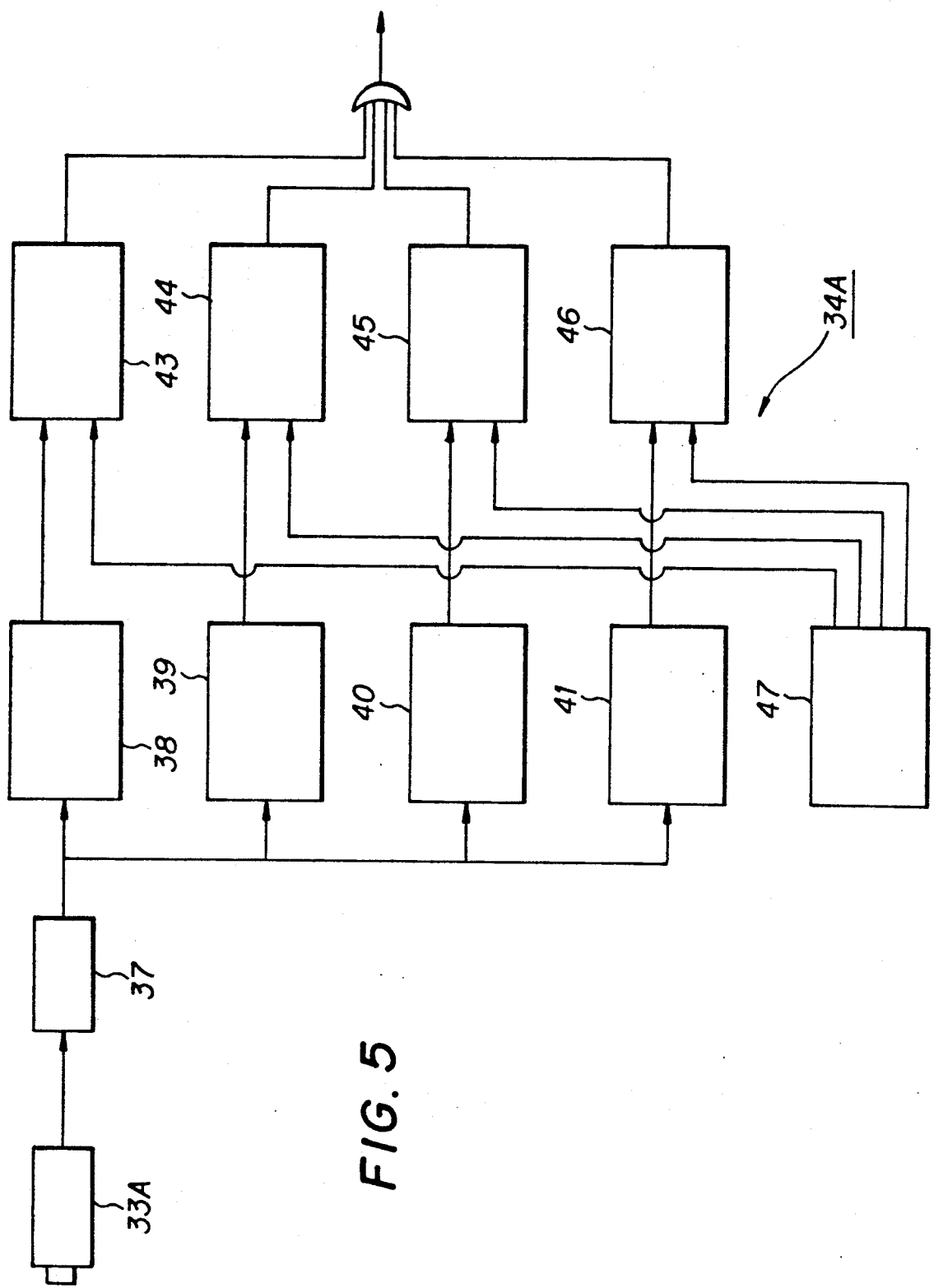

APPARATUS FOR INSPECTING THE PRESENCE OF FOREIGN MATTERS

FIELD OF THE INVENTION

The invention relates to an apparatus for inspecting the presence of foreign matters, and more particularly, to such apparatus which inspects vessels for the presence or not of a foreign matter or matters in a liquid which is filled therein.

DESCRIPTION OF THE PRIOR ART

An arrangement is known in the prior art for inspecting the presence of foreign matters comprising a plurality of receptacles rotatably disposed around a rotatable body and each adapted to receive a vessel to be placed thereon, a rotating mechanism for driving each of the receptacles for rotation in forward or reverse direction, and inspecting means disposed at a given location outside the locus of rotation of the rotatable body for inspecting the vessel for the presence of any foreign matter therein as it is driven for rotation during the rotary motion of the receptacle, the inspecting means being operable to inspect the vessels while the vessels assume an inspecting condition which is reached by a reverse rotation following a forward rotation of the vessels (see Japanese Patent Publication No. 10,466/1972).

In an apparatus of the kind described, a reverse rotation which follows a forward rotation of the vessels which is caused by the rotating mechanism is effective to drive and collect any foreign matter which is mixed into the liquid filling the vessel toward the center of the vessel, thus facilitating the detection of such foreign matter.

In the prior art practice, the rotating mechanism which is used in the apparatus of the kind described comprises a forward rotation friction belt which causes the receptacle to rotate in the forward direction, and a reverse rotation friction belt which is disposed downstream of the forward rotation belt to cause the receptacle to rotate in the reverse direction. With this arrangement, if a change occurs in the speed of rotation of the rotatable body as may be caused by a variation in the speed with which other mechanical units such as a filler or labeller is driven, it causes a corresponding change in the manner of rotating the vessel in the forward or reverse direction, causing a failure of achieving a given, predetermined inspecting condition for the vessel and preventing an accurate inspection for the presence of foreign matters from being achieved.

More specifically, the number of revolutions for the forward or reverse rotation, the time interval over which such rotation is to be maintained or the length of a pause interval between the forward and the reverse rotation generally depend on the size of the vessels, the degree of foaming or the viscosity of the filling liquid, but the allowance for the inspecting condition should be merely within 30% from the most desirable inspecting condition. Hence, if the normal speed of rotation of the rotatable body should be 700 bottles per minute for the number of vessels being processed, for example, a condition which causes the number of processed vessels to be reduced substantially below 500 bottles per minute will depart from the allowance for the inspecting condition, which disables the inspection. However, for a high speed line which processes as many as 700 bottles per minute, a fluctuation in the line speed must be normally allowed from 200 to 700 bottles per minute, which could not have been met by a conventional apparatus for inspecting the presence of foreign matters.

SUMMARY OF THE INVENTION

In view of the foregoing, in accordance with the invention, the rotating mechanism of the apparatus described above comprises a control motor mounted on the rotatable body for driving the receptacle for rotation in the forward or reverse direction, a controller for controlling the control motor and a detector for detecting the speed of rotation of the rotatable body. The controller responds to a signal from the detector by detecting a change in the speed of rotation of the rotatable body, and controls the motor in accordance with such change so that the vessel can be maintained in a predetermined, given permissible inspecting condition in the presence of a change in the speed of rotation of the rotatable body.

With this arrangement, if the speed of rotation of the rotatable body is reduced for some reason, the vessel can be maintained in its given, predetermined permissible inspecting condition as by causing the controller to displace the position at which the forward rotation of the vessel is to be initiated or at which the reverse rotation is to be initiated forwardly, as viewed in the direction of rotation of the rotatable body, thus retarding both the forward and the reverse rotation of the vessel.

If the vessel can be maintained in its given, predetermined permissible inspecting condition in this manner in the presence of a change in the speed of rotation of the rotatable body, it is possible to achieve and maintain an accurate inspection of foreign matters in the presence of appreciable speed changes in the rotation of the rotatable body.

If the size of vessels, the degree of foaming or the viscosity of the filling liquid varies, a different permissible inspecting condition can be readily established. Also a test to determine such permissible inspecting condition is facilitated.

Above and other objects, features and advantages of the invention will become apparent from the following description of an embodiment thereof with reference to the attached drawings.

BRIEF DESCRIPTION OF THE DRAWINGS

FIG..1 is a schematic plane view of one embodiment of the invention;

FIG. 5 is a block diagram of a decision circuit 34A;

DETAILED DESCRIPTION OF EMBODIMENT

Figure 1:
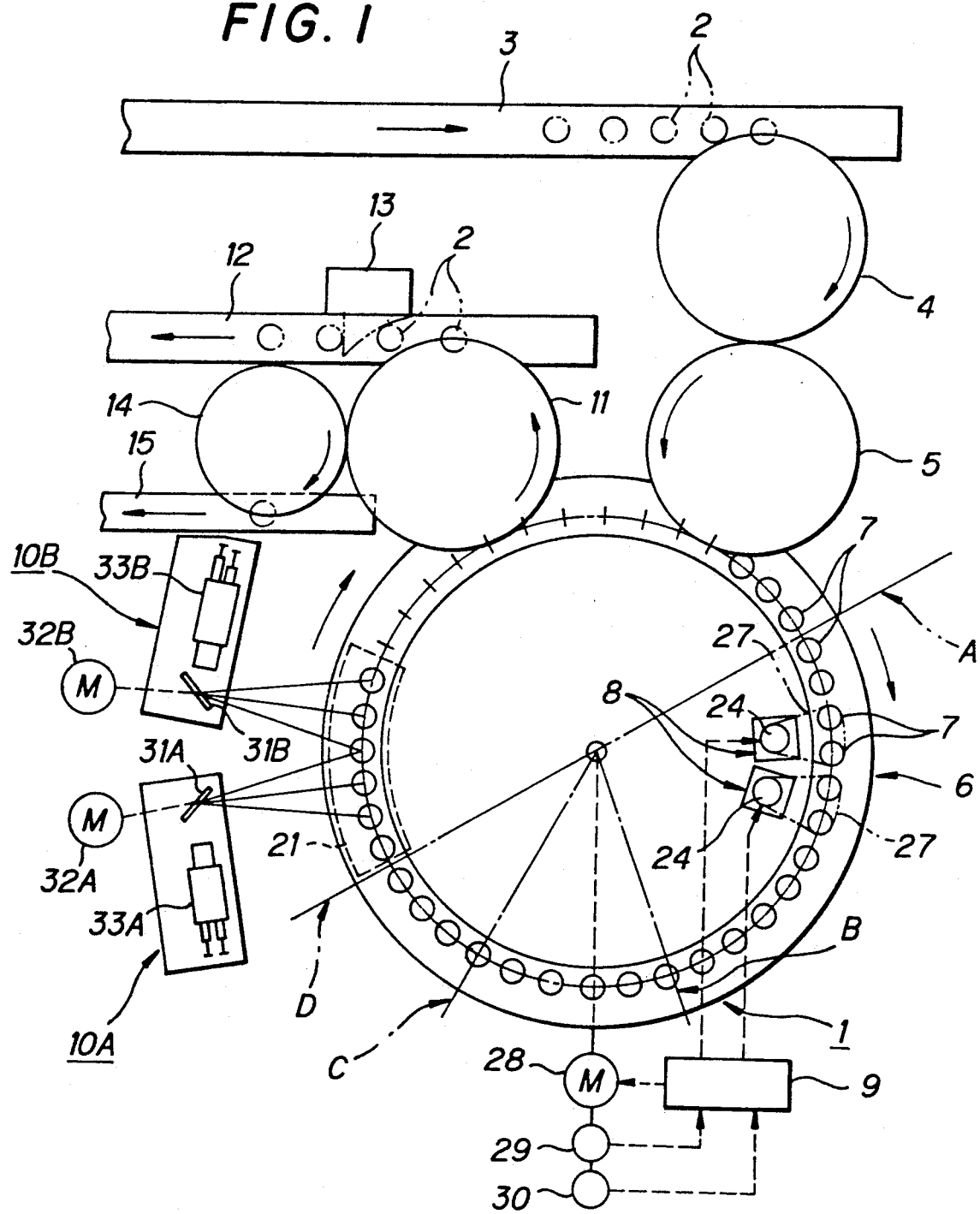

Referring to the drawings, an embodiment of the invention will now be described. In FIG. 1, an apparatus 1 for inspecting the presence of foreign matters is constructed to inspect vessels 2 for the presence of any foreign matter which may be mixed into a liquid which fills them.

After being filled with a liquid, the vessel 2 (see FIG. 2) which has its mouth capped will be sequentially handed from a feed conveyor 3 to a pair of feed star wheels 4, 5, and subsequently is handed over from the wheel 5 to receptacles 7 sequentially which are arranged on a rotatable body 6. As handed over to the receptacles 7, the vessels 2 are conveyed as the rotatable body 6 rotates, and also revolve themselves as the receptacles 7 rotate.

A rotating mechanism 8 is controlled by a controller 9 such that the receptacles 7 begin to rotate clockwise, as viewed in FIG. 1, from a position A, representing the initiation of a forward rotation, and continues to rotate at a given number of revolutions over a given time interval $t_1$ until a stop position B is reached where the rotation of the receptacles is temporarily interrupted for a given time interval $t_2$. After the pause interval $t_2$ passes, the receptacles 7 begin to rotate counter-clockwise at position C, representing the initiation of a reverse rotation, at a given number of revolutions over a given time interval $t_3$ until an inspecting position D is reached where they reach while they undergo a reverse rotation. During their passage through the inspecting position D, a pair of inspecting means 10A, 10B each operate to inspect the vessels 2 if any foreign matter is mixed into a liquid which fills them.

Figure 4:
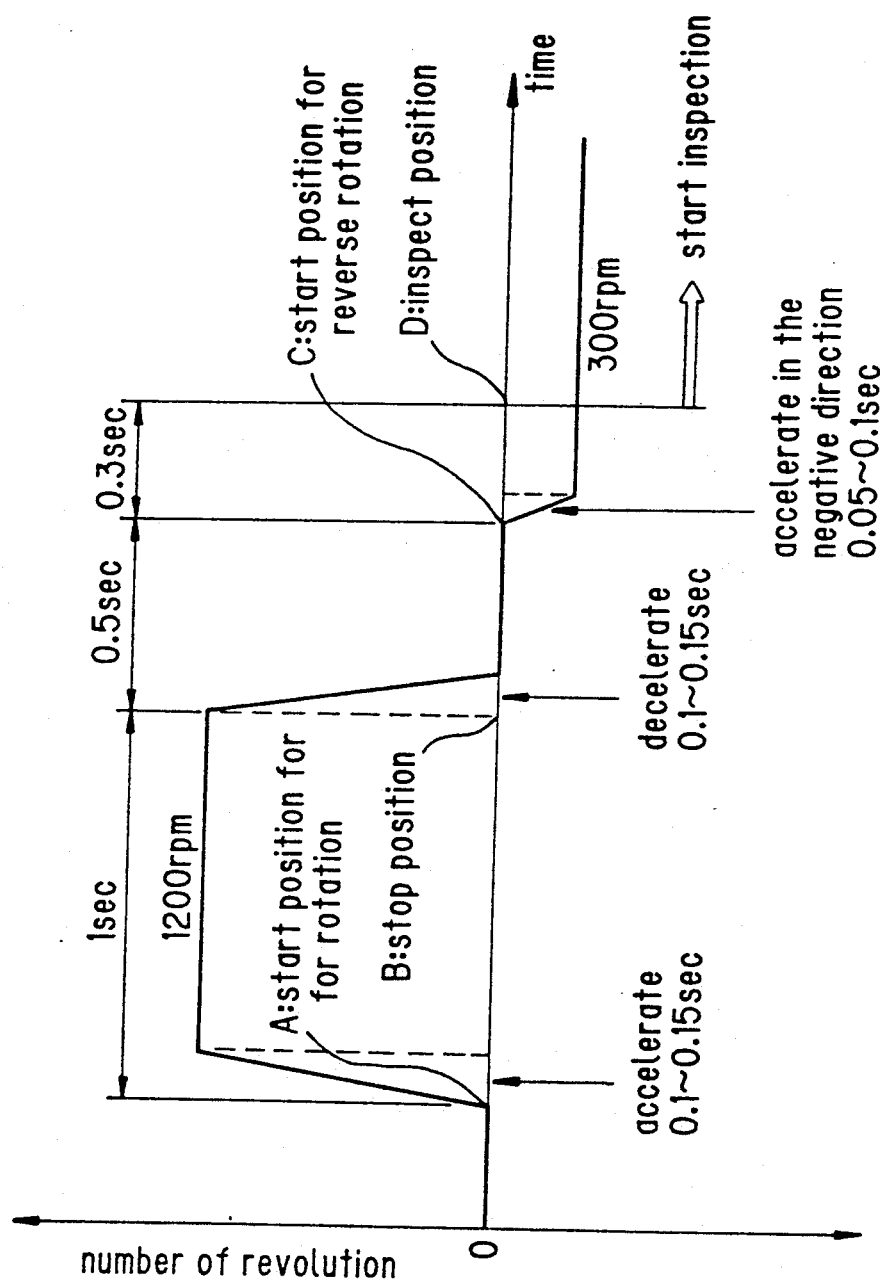
FIG. 4 is a diagram showing a specific example of control over the rotation of a receptacle 7.

A specific example of control over the rotation of the receptacle 7 is illustrated in FIG. 4. Referring to this Figure, the time interval $t_1$ which is required for the receptacle 7 to move from the forward rotation initiation position A to the stop position B is illustrated as 1 second, the time interval $t_2$ required to move from the stop position B to the reverse rotation initiation position C 0.5 second, and the time interval $t_3$ required to move from the position C to the inspecting position D 0.3 second.

When the receptacle 7 reaches the position A, it is accelerated at a predetermined, constant acceleration from its standstill condition to a number of revolutions equal to 1,200 rpm over an interval of about 0.1 to 0.15 second, and subsequently continues to rotate at a constant rate of 1,200 rpm. When the receptacle 7 subsequently reaches the stop position B, it is decelerated at a constant, predetermined deceleration from 1,200 rpm to its standstill condition over a time interval of about 0.1 to 0.15 second, and subsequently remains at rest. Finally, when the receptacle 7 reaches the position C, it is accelerated at a constant, predetermined acceleration in the reverse direction from its standstill condition to 300 rpm over a time interval of about 0.05 to 0.1 second, and subsequently continues its rotation at a constant rate of 300 rpm. It passes through the inspecting position D while continuing such rotation.

In this manner, by causing the receptacle 7 to rotate in one direction to induce a significant rotation of the liquid which fills the vessel 2, and then ceasing the rotation of the receptacle 7, any foreign matter which may be mixed into the filling liquid may be shifted toward the center of the vessel. Subsequently, the reverse rotation is effective to reduce the length of time required for the foreign matter to shift toward the center as such shift is caused by the interruption of the rotation.

When the pair of inspecting means 10A, 10B reveal a positive result of inspection for the vessel 2, meaning that the vessel has a normal content, such vessel may be delivered by a delivery star wheel 11 onto a delivery conveyor 12. However, any vessel 2 which is found to be defective will be diverted by a rejector 13 to be conveyed by the rotation of the delivery star wheel 11 to a position beyond the delivery conveyor 12, and is then handed over to a reject wheel 14 to be delivered onto a reject conveyor 15 as a defective product. The rejector 13 is well known in the art, and therefore will not be specifically described.

Figure 2:
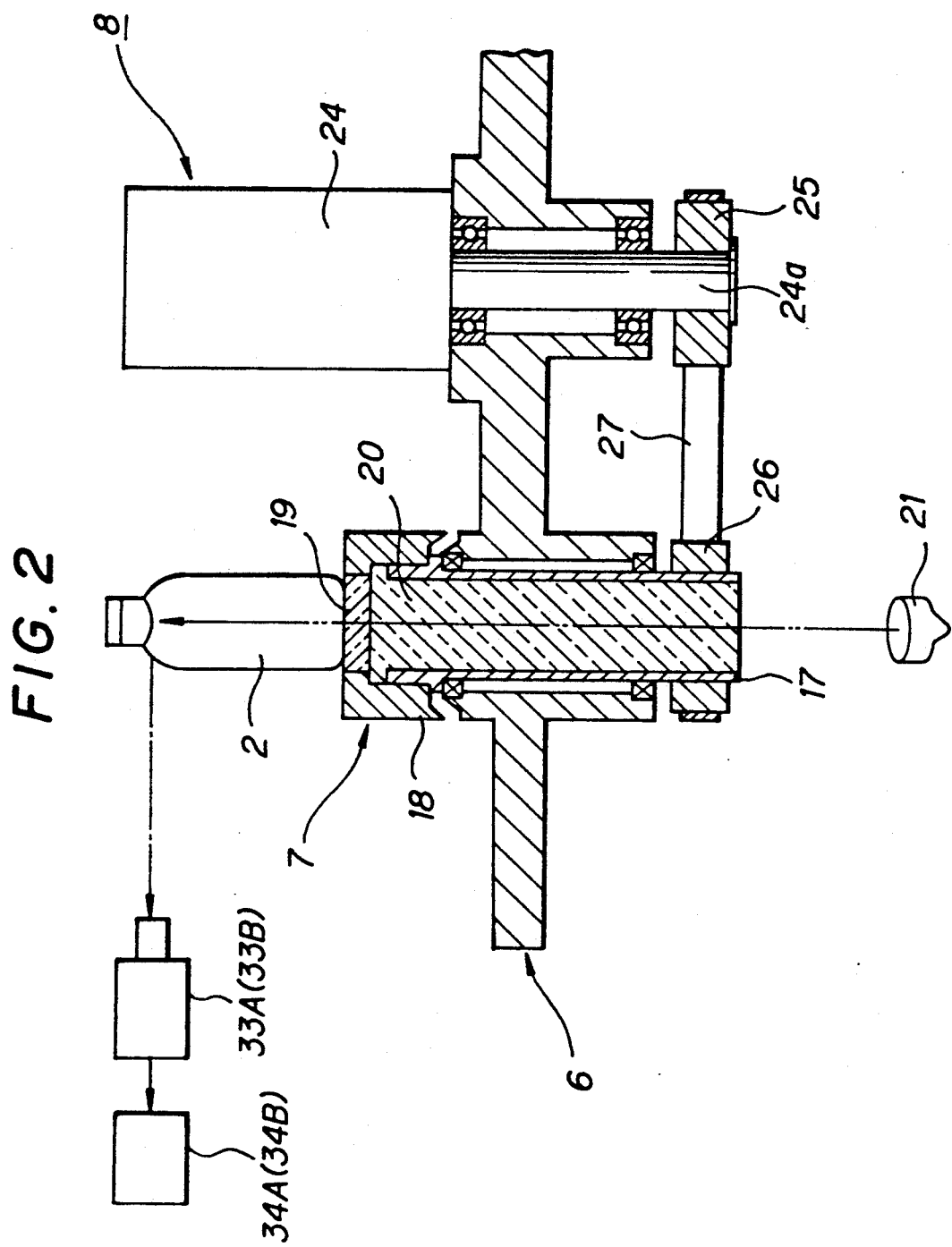
FIG. 2 is a schematic view, partly in section, of part of the arrangement shown in FIG. 1.

The receptacles 7 are mounted on the rotatable body 6 along its outer periphery at an equal circumferential interval. As shown in FIG. 2, each receptacle 7 is mounted on the top end of a hollow rotary shaft 17 which is vertically disposed and journalled on the rotatable body 6. Each receptacle 7 includes a cylindrical holder 18 which is secured to the upper end of the rotary shaft 17, a transparent support plate 19 fitted in the axial portion of the holder 18 for carrying a vessel 2 thereon, and a light transmitting member 20 which is disposed in the hollow interior of the rotary shaft 17. The member 20 may be formed of clear acryl, for example, and acts to enable an efficient transmission of light emitted by a light source 21 to the vessel 2.

The rotating mechanism 8 which drives the receptacles 7 for rotation comprises a control motor 24 mounted on the rotatable body 6 and having its drive shaft 24a directed vertically downward, a belt wheel 25 mounted on the drive shaft 24a, another belt wheel 26 mounted on the bottom of the rotary shaft 17, and a belt 27 running across the belt wheels 25, 26. As shown in FIG. 1, the belt 27 extends around the belt wheel 26 of two adjacent receptacles 7, whereby two receptacles 7 can be simultaneously driven for rotation in the same direction by a single control motor 24.

The operation of each control motor 24 is controlled by the controller 9 so as to drive the receptacles 7 for rotation under the operating conditions mentioned above. The controller 9 also controls the operation of a control motor 28 which is mechanically coupled to the rotatable body 6. Specifically, the controller 9 causes the rotatable body 6 to be continuously driven for rotation clockwise, as viewed in FIG. 1, and an angular position of the rotatable body 6 is detected by a rotary encoder 29 which is coupled to the control motor 28 while the speed of rotation of the rotatable body 6 is detected by a tachometer 30. Obviously, both the angular position and the speed of rotation of the rotatable body 6 may be detected by a single detector.

The pair of inspecting means 10A, 10B disposed at the inspecting position D comprises tracking mirrors 31A, 31B which are angularly driven to track the vessels 2 as they are conveyed by the rotation of the rotatable body 6, and control motors 32A, 32B which operate as mirror drive means for angularly driving the respective tracking mirrors 31A, 31B counter-clockwise, as viewed in FIG. 1, in following or tracking relationship with the movement of the vessels 2 from their given start position and for quickly returning them to the start position by an angular drive in the opposite or clockwise direction as soon as a given end position is reached. A picture of the vessel 2 which forms on each of the tracking mirrors 31A, 31B can be photographed by respective video cameras 33A, 33B.

Figure 3:
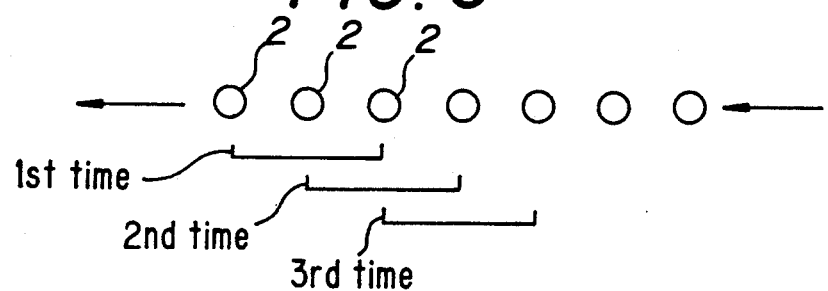
FIG. 3 is a schematic view illustrating a tracking operation of tracking mirrors 31A, 31B.

As schematically illustrated in FIG. 3, in the present embodiment, each of the tracking mirrors 31A, 31B and the video cameras 33A, 33B is capable of taking four photographs of three vessels during the tracking operation. In addition, when the tracking mirrors 31A, 31B are quickly returned from the end position to the start position to track the three vessels 2 again, such vessels are those which are by one vessel displaced rearwardly, as viewed in the direction of conveyance.

Accordingly, one inspecting means 10A performs three tracking operations upon a single vessel 2, and takes four pictures during its tracking operation, thus yielding a total of twelve pictures. The other inspecting means 10B operates similarly. Accordingly, a total of twenty-four pictures can be obtained for a single vessel 2.

It is to be noted that the tracking mirrors 31A, 31B are reciprocatively driven for rotation over a tracking zone which is substantially identical to that required to track a single vessel 2, so that the length of the tracking zone for the mirrors can be reduced and a resulting distortion of the picture which may be caused by an increased length of the tracking zone may be reduced, as compared with an arrangement in which three vessels are tracked to provide a total of twelve pictures and then the mirrors are quickly returned to the start position to track three fresh or different vessels.

Signals from the video cameras 33A, 33B are input to decision circuits 34A, 34B (FIG. 2). Each decision circuit 34A, 34B is identical in construction and therefore only decision circuit 34A will be described. Referring to FIG. 5, an analog signal from the video camera 33A is converted into a digital signal by an A/D converter 37, and is then input to four binary conversion circuits 38, 39, 40, 41 in the present embodiment.

Each of the binary conversion circuits 38 to 41 operates to derive a binary value from the digital signal on the basis of a preset reference value. Accordingly, the picture of the three vessels 2 can be converted into a binary value on the basis of each reference value or required sensitivity.

The signals which are obtained by the binary conversion circuits 38 to 41 are fed to a liquid vessel elevation decision circuit 43, and three or top, middle and bottom foreign matter decision circuits 44, 45, 46, respectively, and each of the decision circuits 43 to 46 also receives a signal from an inspection area selector 47 which designates a particular inspection area.

Figure 6:
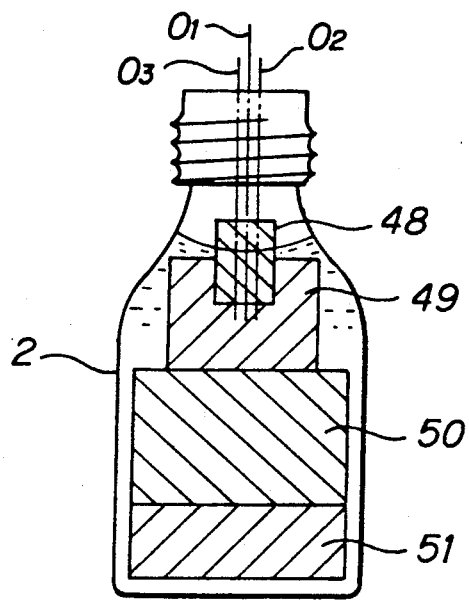
FIG. 6 is a pictorial illustration of inspection areas 47 to 51 which are established by an inspection area selector 47.

The inspection area selector 47 establishes given inspection areas for each of the three vessels 2 which are photographed simultaneously. Referring to FIG. 6, the inspection area selector 47 feeds a liquid level area 48, which represents a region within the vessel 2 corresponding to the level of the filling liquid, to the liquid level elevation decision circuit 43, feeds a top area 49, corresponding to the top portion of the filling liquid from which the area 48 is excluded, to the top foreign matter decision circuit 44, feeds a middle area 50, representing the middle portion of the filling liquid, to the middle foreign matter decision circuit 45, and feeds a bottom area 51, representing the bottom portion of the filling liquid, to the bottom foreign matter decision circuit 46. It is to be noted that the areas 48 to 51 are chosen to overlap slightly each other.

The liquid level elevation decision circuit 43 extracts a signal for the liquid level area 48 which is preset by the selector 47, from the binary signal derived by the binary conversion circuit 38, and compares the extracted signal or a detection value obtained therefrom against a predetermined reference value to determine if the liquid level of the vessel lies at a given elevation.

Figure 7:
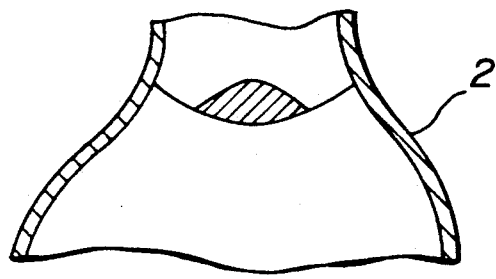
FIG. 7 is a pictorial illustration of the inspection of the liquid level elevation of a non-foaming filling liquid.
Figure 8:
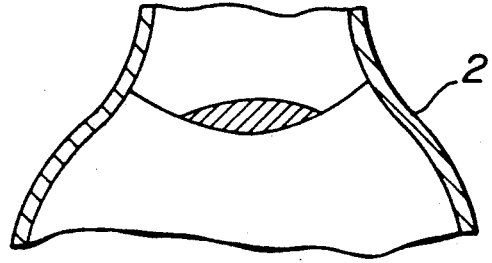
FIG. 8 is a similar pictorial illustration for a foaming filling liquid.

The predetermined reference value used in the decision circuit 43 is chosen on the basis of a curved liquid surface. Thus, when the vessel is caused to rotate to produce a curved liquid surface in the filling liquid, a generally diamond-shaped brightening portion forms in a less foaming filling liquid (see FIG. 7) while a generally disc-shaped brightening portion will form in a more foaming filling liquid since in this instance, a bubble region disposed above the liquid surface will tend to be brightened more strongly (see FIG. 8). Accordingly, the brightening portion is previously determined in accordance with the variety of the filling liquid and the speed of rotation, and the elevation of the middle of the brightening portion, for example, may be chosen as a reference value.

When detecting the elevation of the middle of the brightening portion from the extracted signal, the elevation of the middle of the brightening portion is detected along a vertical line $O_1$ shown in FIG. 6 which is aligned with the axis of the vessel 2 and along two adjacent vertical lines $O_2$ and $O_3$, and a decision that a proper liquid level elevation is reached is rendered if at least one of the detected values coincides with the reference value. The purpose of such choice compensates for the fact that the center of the curved surface does not always coincide with axis of the vessel 2 due to the oscillation of the curved surface.

Each of the top, the middle and the bottom foreign matter decision circuit 44, 45 and 46 operates to extract signals representing the respective areas 48 to 50 chosen by the selector 47, from the binary signal which is derived by the binary conversion circuits 39 to 41, respectively, at different sensitivities, and compares the extracted signal against a predetermined reference value to determine if any foreign matter is contained in the filling liquid.

In the present embodiment, the binary conversion circuit 39 is chosen to exhibit a lowered sensitivity to avoid a false detection inasmuch as bubbles tend to form in the top area 48. Glass or metal pieces may precipitate in the bottom area 51, and accordingly the binary conversion circuit 41 is chosen to exhibit a higher sensitivity to improve the accuracy of detection. The binary conversion circuit 40 corresponding to middle area 50 exhibits a sensitivity which is intermediate the both sensitivities.

In each of the decision circuits 34A and 34B, the respective decision circuits 43 to 46 renders a decision twelve times upon a single vessel 2. If an abnormality is detected in one of these detections, an abnormality detection signal which is then produced actuates the rejector 13.

In the described arrangement, when the rotatable body 6 is rotating at its normal running speed, the operation of the receptacles 7 are controlled, in pairs, by the rotating mechanism 8 in the manner illustrated in FIG. 4. By contrast, when the rotatable body 6 runs at a lower speed, the controller 9 detects the angular position and the speed of rotation of the rotatable body 6 by means of the rotary encoder 29 and the tachometer 30, and calculate a new position A, representing the initiation of the forward rotation, a new stop position B and a new position C, representing the initiation of the forward rotation, in accordance with the speed of rotation of the rotatable body 6 in order to achieve the condition illustrated in FIG. 4.

In this instance, the positions A, B and C will be retarded relative to those positions which will be assumed when the rotatable body 6 runs at its normal speed, or these positions will be displaced forwardly as viewed in the direction of rotation of the rotatable body. By calculating the new positions A, B and C properly, the condition as illustrated in FIG. 4 can be maintained as when a normal speed of rotation of the rotatable body is maintained. However, it should be noted that only the position A for the initiation of the forward rotation may be calculated while the stop position B and the position C for the initiation of the reverse rotation may be determined by watching the time elapsed after the position A is reached.

When the rotatable body 6 is set in motion after it has once been stopped by an emergency stop, a vessel which has come to a stop at a position immediately before the inspecting position D, for example, may be compensated for by causing the rotating mechanism 8 to control the rotation of the receptacle 7 so that the condition illustrated in FIG. 4 is achieved before resuming the operation of the rotatable body 6. By timing the resumption of the operation of the rotatable body with the achievement of the condition illustrated in FIG. 4, the number of vessels which must be rejected as a result of a failure of the inspection may be reduced.

The control motors 24, 28, 32A and 32B may comprise servo motors, stepping motors or inverter motors with brakes as desired. While the acceleration and the deceleration applied when rotating the receptacles 7 have been maintained constant in the embodiment illustrated above, it should be understood that they may also be changed provided a given, predetermined permissible inspecting condition can be obtained.

While the invention has been disclosed above in connection with a preferred embodiment thereof, it should be understood that a number of changes, modifications and substitutions will readily occur to one skilled in the art from the above disclosure without departing from the spirit and scope of the invention as defined by the appended claims.

What is claimed is:

1. An apparatus for inspecting a presence of foreign matters including a plurality of receptacles rotatably disposed around a rotatable body for receiving vessels to be placed thereon, a rotating mechanism for driving the respective receptacles for rotation in a forward and a reverse direction, and inspecting means disposed at a given station outside the rotatable body for inspecting the vessels for the presence of any foreign matter therein as they are driven by the rotation of the receptacles, the inspecting means inspecting the vessels during an inspecting condition thereof which is reached by a reverse rotation which follows a forward rotation thereof;

wherein the rotating mechanism comprises a control motor mounted on the rotatable body for driving the receptacle for rotation in the forward and the reverse direction, a controller for controlling the control motor, and a detector for detecting the speed of rotation of the rotatable body, the controller responding to a signal from the detector to detect any change in the speed of rotation of the rotatable body so as to control the control motor in accordance with such change, thereby allowing a given, predetermined permissible inspecting condition of the vessel to be maintained if the speed of rotation of the rotatable body changes.

2. An apparatus according to claim 1 in which the control motor is effective to drive the receptacle for rotation in the forward direction, then stops it and then drives it for rotation in the reverse direction.

3. An apparatus according to claim 1 in which each of the receptacles is mounted on the top end of a hollow rotary shaft which is vertically journalled on the rotatable body, the rotary shaft including a hollow portion through which light from a light source is transmitted to a vessel placed on the receptacle.

4. An apparatus according to claim 3 in which a clear light transmitting member is disposed in the hollow portion of the rotary shaft.

5. An apparatus according to claim 1, further including a tracking mirror disposed to track the movement of a vessel, mirror drive means for causing the tracking mirror to track the vessel as it is conveyed by the rotatable body from a start position to an end position whereupon the mirror is quickly returned to the start position, and a video camera for photographing the vessel during the time the tracking mirror tracks the vessel, the video camera being operable to take a picture of a plurality of vessels as the tracking mirror tracks the vessels, the mirror drive means causing the tracking mirror to track a plurality of vessels during a current pass in a manner such that at least the rearmost one of the vessels which were tracked during a previous pass is contained therein.

6. An apparatus according to claim 1, further including a video camera for taking a picture of vessels as they are conveyed by the rotatable body, and a decision circuit responsive to a picture taken by the video camera and a predetermined reference value to determine if a liquid which fills the vessel has a proper liquid level elevation, the reference value used in the decision circuit being chosen on the basis of a curved liquid surface which is produced within the vessel as the receptacle rotates.

7. An apparatus according to claim 1, further including a video camera for taking a picture of vessels as they are conveyed by the rotatable body, and a decision circuit for comparing a picture taken by the video camera against a predetermined reference value to determine if the vessel is proper or not, the decision circuit including a first decision circuit which compares one area of the picture taken by the video camera against a first reference value, and a second decision circuit which compares another area of the picture taken by the video camera against the second reference value.

* * * * *